United States Patent [19]

Clendenning

[11] Patent Number: 5,211,642

[45] Date of Patent: May 18, 1993

[54] CHAMBERS DRAINAGE SYSTEM

[76] Inventor: Beverly F. Clendenning, 8 Trinity La., Blackwood, N.J. 08012

[21] Appl. No.: 783,330

[22] Filed: Oct. 28, 1991

[51] Int. Cl.⁵ .............................................. A61M 1/00
[52] U.S. Cl. .................... 604/410; 604/408; 604/317; 604/322; 604/326
[58] Field of Search ............ 604/317, 322, 326, 349, 604/407, 408, 410, 27, 28, 48, 49, 54, 93, 257, 260, 262

[56] References Cited

U.S. PATENT DOCUMENTS

| 3,001,565 | 9/1961 | Beach | 604/326 |
|---|---|---|---|
| 3,058,799 | 10/1962 | Rowles, Jr. | 604/410 X |
| 3,832,999 | 9/1974 | Crilly | 128/275 |
| 4,417,892 | 11/1983 | Meisch | 604/349 X |
| 4,465,484 | 8/1984 | Cianci | 604/317 |
| 4,505,703 | 3/1985 | Gale et al. | 604/317 |
| 4,551,141 | 11/1985 | McNeil | 604/317 |
| 4,564,361 | 1/1986 | Akiyama | 604/265 |
| 4,723,950 | 2/1988 | Lee | 604/322 |
| 4,786,286 | 11/1988 | Cerny et al. | 604/406 |
| 4,854,737 | 8/1989 | Steer et al. | 383/127 |
| 4,936,837 | 6/1990 | Wexler et al. | 604/326 |

FOREIGN PATENT DOCUMENTS

| 940791 | 1/1974 | Canada | 604/408 |
|---|---|---|---|
| 1358380 | 7/1974 | United Kingdom | 604/408 |

Primary Examiner—Robert A. Hafer
Assistant Examiner—Sam Rimell
Attorney, Agent, or Firm—Thomas A. Lennox

[57] ABSTRACT

A system and method is provided to handle the fluids issuing from a patient's bladder after a prostate operation utilizing continuous bladder irrigation eliminating any antireflux valve system and connecting a ten liter overflow drainage bag of at least ten liters in capacity or a pair of bags directly to the drainage spout of the standard urinary drainage bag providing a closed system with open drainage all the way to the overflow drainage bag.

13 Claims, 2 Drawing Sheets

CHAMBERS DRAINAGE SYSTEM

BACKGROUND OF THE INVENTION

This invention involves a chambers drainage system and in particular the handling, collection and storage of fluids issuing from a transurethral catheter device inserted in a patient after a transurethral resection procedure or a bladder tumor removal to provide continuous bladder irrigation.

After the increasingly common prostate operation and other operations, it is necessary to employ continuous bladder irrigation for a number of hours up to a couple of days after the operation. The transurethral "three-way" catheter insertion after a resection is a common procedure and a number of companies supply the equipment for insertion, inflation to retain the catheter, and connection to a collection bag, typically a four liter flexible plastic film bag, all called a "Foley" apparatus. After the operation, it is necessary to continue bladder irrigation until the fluids run clear, that is without any blood present. In the early stages of irrigation, immediately after the operation, there is substantial blood in the fluid which, over a period of time, continues to lighten in intensity until the fluid is clear. The fluid collected may be up to about three liters per hour. Immediately after the operation it is necessary that a nurse check, measure the flow, and empty the four liter urinary drainage bag about every quarter hour. If this emptying procedure is missed, there is a back up of fluids causing pressure on the prostate fossa resulting in bladder distention and bladder spasms. This frequently requires manual irrigation and increases the possibility of infection. In some cases, the transurethral apparatus has to be removed and a new one inserted causing trauma to the prostate fossa with increased bleeding, spasms and clots. In order to avoid the possibility of back up, the supliers of the urinary drainage bag have included an antireflux valve to prevent back flow to the patient when the bag fills. This has long since been determined unsatisfactory as there is substantial blood clotting in the antireflux valve clogging the flow and requiring reinsertion of a new apparatus. This particularly occurs in the early stages after the operation, when a substantial amount of blood and small clots quickly restrict the flow and cause immediate failure of the system at a stage when the patient is particularly vulnerable.

The doctors have recognized that this is an unsatisfactory situation and for a period of more than ten years have employed the system illustrated in FIG. 1. As illustrated in FIG. 1, the transurethral catheter apparatus 10 used in the procedure empties through tube 12 into standard urinary drainage bag 14. Most TURP devices include an antireflux valve in the fluid flow line of tube 12. Bag 14 will hold about four liters and is equipped with exit drainage tube 18 supplied with closure clamp 16. In order to reduce spillage, when the open system is used, tube 18 is attached with adhesive tape to the top edge of open bucket with closure valve 16 wide open. As noted above, any antireflux valve 20 present in tube 12 has been made inoperable to obtain as free a flow as possible. Attempts to construct a lid to cover the bucket and still allow the tube to be held securely while maintaining an air tight system were unsuccessful. This open system has the advantage of essentially eliminating the possibility of a backup and failure of the drainage system. It has the additional advantage that the amount of saline solution used in the continuous bladder irrigation may be increased with minimal concern for the volume of fluids used that would too quickly fill up urinary drainage bag 14. However, other problems and complications arise from the use of this open system. Using the prior art device with the open collection container, every minor spill convinces the patient that it is an overflow causing substantial emotional upset. With a free spout, no matter what the connection means to the open bucket, it is virtually impossible to avoid sudden movement of the spout dislodging it and causing it to drop to the floor. When fluids are spilled, it is impossible to measure the amounts of fluid increasing the risk that the patient may be retaining fluids caused by a clot. The open container which contains urine emits a rank odor and the stench increases as the fluid is collected. Further, there is almost always a residue in the bottom of the bucket which makes cleaning difficult. The open container is unsightly to the patient and family members visiting the patient. In fact, the visitors walking down the hallway are nauseated by the display. In addition, the constant draining sound into the bucket over a period of hours causes anguish to the patient as compared to the closed system where the stream cannot be heard. Of particular concern is that the open drainage system increases the chance of infection from bacteria entering the open system to a fresh postoperative patient. Finally, no matter what precautions are taken, there is a substantial risk of spillage from the bucket causing a wet floor and intense housekeeping problems. Rugs are not practical and a tile floor after any spillage presents a high risk of a slip and fall.

Despite this procedure being utilized for over a decade, no answer has been provided and none of the devices described in the prior art satisfy these needs nor attain the objects described hereinbelow.

SUMMARY OF THE INVENTION

It is an object of the present invention to provide a chamber drainage system that avoids essentially all of the problems associated with the various attempts to handle the drainage fluids described hereinabove. In particular, although closed drainage systems have been used in the past, a closed drainage system utilizing an essentially limitless collection capacity has not been used. An important aspect of the present invention is the utilization of a large closed overflow drainage bag positioned below the standard urinary drainage bag and providing free flow all the way from the patient to the overflow storage bag. Providing free flow includes incorporating no antireflux valve in the system or, in the alternative, disabling any existing antireflux valve providing essentially free flow through that valve mechanism.

It is a particular object of the present invention to provide a system that avoids almost any risk of spillage and also is a closed system to avoid introduction of bacteria from the air.

It is an additional object of the present invention to provide a system and a device that essentially prevents backup or clogging which would prevent free flow of the fluids from the patient's bladder thus avoiding bladder distention and bladder spasms.

It is a particular object of the present invention to provide a free flow system which avoids blood clotting in the system which might restrict flow.

It is a further object of the present invention to provide a system and method that can utilize increasing amounts of fluid introduction in the continuous bladder irrigation procedure.

It is a specific object of the present invention to reduce the stench from open drainage systems, reduce the unsightly appearance of the device and method and essentially eliminate the sound of the draining procedure which causes anguish after a period of time for the patient. The system of the present invention can be easily covered or merely positioned under the chair or the bed of the patient to place the system out of sight.

It is an additional object of the present invention to provide a catheter drainage system which will allow easy access to observe the color of the fluids issuing from the bladder and to enable the nurse to make a decision to increase or decrease the rate of irrigation.

It is a further object of the present invention to provide a catheter drainage system which allows easy removal of the collected fluids without ever opening the system to the atmosphere.

It is a specific object of the present invention that when continuous bladder irrigation is terminated, the chamber device of the present invention may be disconnected and the standard Foley device used to collect urine without ever opening the system to the atmosphere.

An aspect of this invention is a method of collecting fluids drawn from a patient's bladder using a transurethral catheter procedure. The method includes inserting transurethral catheter means into the patient to continuously irrigate the bladder of the patient and to continuously drain fluids from the bladder. The method further includes connecting an inlet tube of a urinary drainage collection device to the transurethral catheter means. The urinary drainage collection device includes a collection bag to receive and hold a volume of fluids, the inlet tube connected to a drainage outlet opening to the collection bag, and first closure means to open and close flow through the drainage tube. The method further includes providing that there is no antireflux device in the urinary drainage collection device to provide as high unobstructed flow as possible into the collection bag of the urinary drainage collection device. The method also includes providing a storage bag that includes a closed air tight capacity of at least about eight liters, a second inlet tube connected to an inlet opening in the storage bag, a second drainage tube connected to a drainage outlet opening from the storage bag, and second closure means to open and close flow through the second drainage tube. The method further includes connecting the second inlet tube of the storage bag to the first drainage tube of the collection bag using connecting means to connect ends of the tubes in an essentially leak proof connection. The method also includes positioning the storage bag at a height below the collection bag, and continuously irrigating the bladder until the fluids no longer show the presence of blood.

It is preferred that the drainage collection bag have a capacity of eight to twelve liters. It is most preferred that the drainage collection bag have a capacity of about ten liters. It is further preferred that the connecting means to connect ends of the first inlet tube of the storage bag and the first drainage tube of the collection bag be a 5:1 tube connector. It is further preferred that the method further include closing the first closure means to prevent flow through the second drainage tube, raising support the storage bag to a chosen height, opening the second closure means to drain the accumulated fluids through the second drainage tube, measuring the quantity of the fluids drained from the storage bag, closing the second closure means to prevent flow through the second drainage tube, and opening the first closure means to allow flow through the second drainage tube. It is further preferred that the method further include at the closing of the second closure means to prevent flow through the second drainage tube, thus retaining a sufficient quantity of fluids in the second drainage tube to fill a section of the second drainage tube.

Another aspect of the invention is a device for collecting fluids drawn from a patient's bladder using transurethral catheter means insertable into the patient to continuously irrigate the bladder of the patient and to continuously drain fluids from the bladder. The device includes a urinary drainage collection device that includes a collection bag to receive and hold a volume of fluids, an inlet tube connected to an inlet opening to the collection bag and connectable to the transurethral catheter means, a first drainage tube connected to a drainage outlet opening to the collection bag and connectable to the transurethral catheter means, a first drainage tube connected to a drainage outlet opening the collection bag, and first closure means to open and close flow through the drainage tube. The urinary drainage collection device includes no antireflux means to prevent liquid flow from the urinary drainage collection device to the transurethral resection means to provide unobstructed flow into the collection bag of the urinary drainage collection device. The device further includes connection means to connect the inlet tube of the urinary drainage collection device to the transurethral catheter means. The device also includes a storage bag device that includes a closed air tight storage bag of a capacity of at least about eight liters, a second inlet tube connected to an inlet opening in the storage bag, a second drainage tube connected to a drainage outlet opening from the storage bag, and second closure means to open and close flow through the second drainage tube. The device further includes second connection means to connect open ends of the second inlet tube of the storage bag and the first drainage tube of the collection bag in an essentially leak proof connection.

It is preferred that the drainage collection bag have a capacity of at least about ten liters. It is further preferred that the device include means to hang the storage bag at a height above the floor. It is also preferred that the storage bag further include a first edge and the inlet and outlet openings of the storage bag open proximate to the first edge, and the device further include means to hang the storage bag at a height above the floor with the first edge at the bottom. It is further preferred that the storage bag further include graduated markings indicating increasing fluid volume levels in the storage bag from the first edge to an opposite edge of the storage bag. It is also preferred that the second connecting means to connect ends of the inlet tube of the drainage collection bag and the drainage tube of the collection bag be a 5:1 tube adapter.

It is preferred that the drainage collection bag have a capacity of about eight to about fifteen liters and more preferably about twelve liters. It is also preferred that the connecting means to connect ends of the inlet tube of the drainage collection bag and the drainage tube of the collection bag be a 5:1 tube adapter.

DESCRIPTION OF PREFERRED EMBODIMENTS

Figure 1:
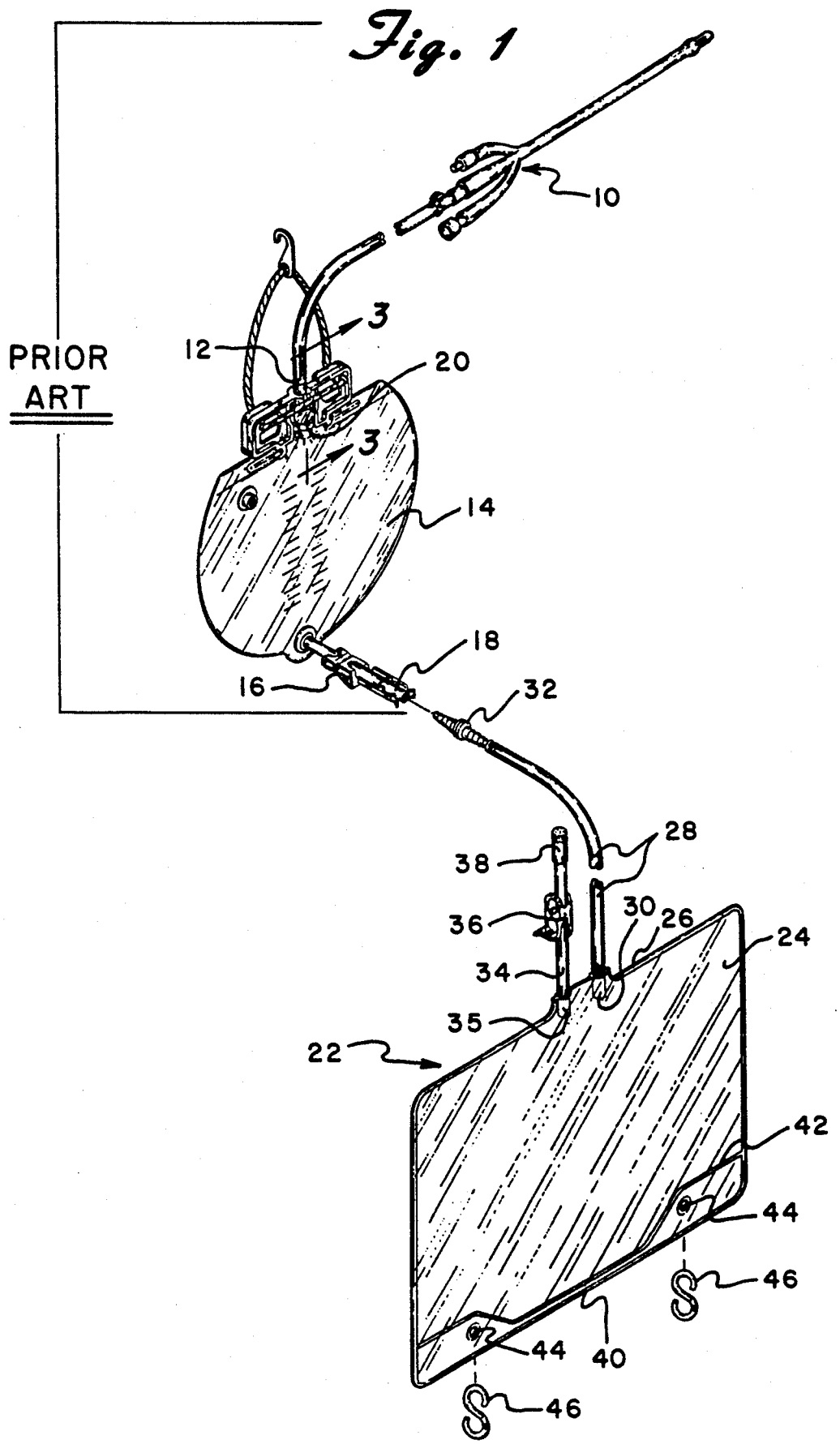
FIG. 1 is a perspective view of a chamber drainage system of the present invention coupled with the prior art Foley apparatus.

Coupled to the prior art Foley catheter device is chamber drainage apparatus 22 illustrated in FIG. 1. Apparatus 22 includes ten liter flexible plastic collection bag 24 with a twelve liter capacity. Bag 24 is constructed using standard heat sealing techniques around the edges of plasticized polyvinyl chloride film panels with chemical resistance to withstand the various fluids being collected. Bag 24 is connected through flexible plastic tubing 28 to exit tube 18 using plastic molded connector 32. Connector 32 is known in the trade as a "Five in One Connector" supplied by Barter Health Care Corporation of Valencia, Calif., Product No. 350A, as it is used to connect various sized tubing and components in at least five different uses. Inlet opening 30 to bag 24 is positioned along top edge 26. Drainage tube 34 is connected to drainage opening 35 also located along top edge 26. Spring clamp 36 closes tube 34 and plastic molded cap 38 slides over the open end of tube 34 to prevent any inadvertent dripping. Along bottom edge 40 reinforcement panel 42 provides added strength around holes 44 which pass through both sides of bag 24 and are sealed to prevent any leakage. "S" hooks 46 are provided to allow bag 24 to be hung up using hooks 46 inverted for drainage of fluids through tube 34.

Figure 2:
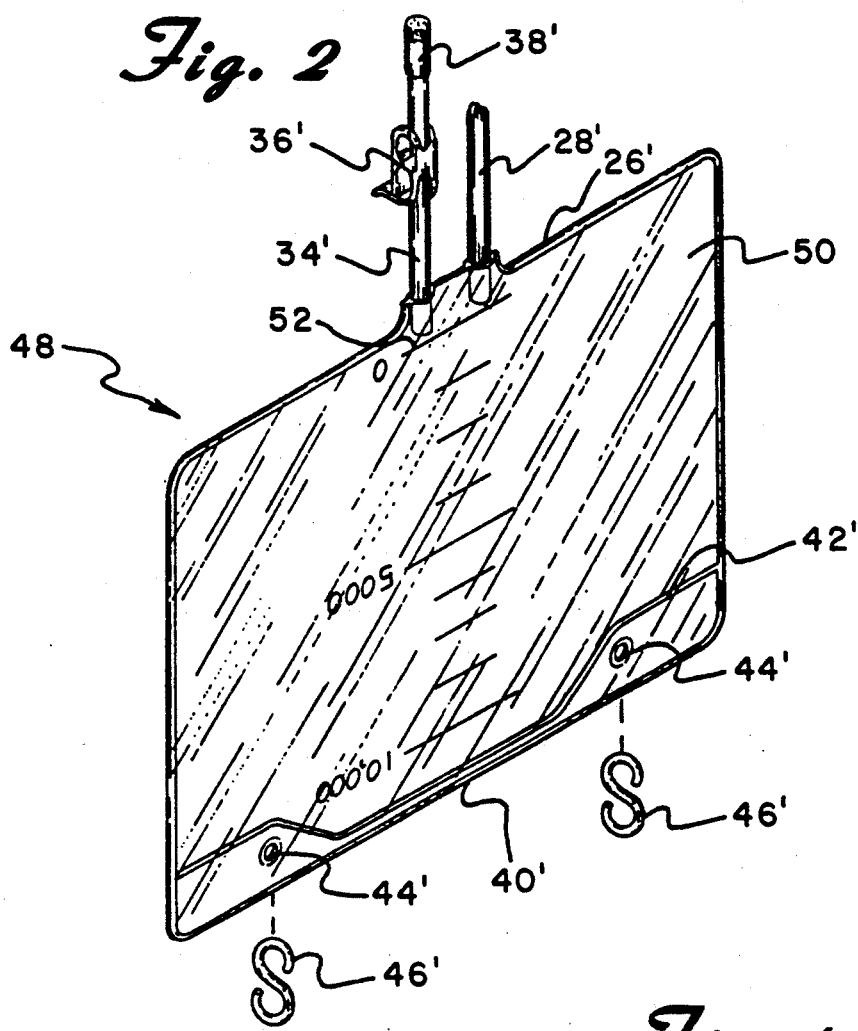
FIG. 2 is a perspective view of a second embodiment of a chamber drainage device of the present invention.

In FIG. 2, a second embodiment device 48 includes flexible bag 50, which is essentially identical to bag 24 except that it has a volume capacity of ten liters and graduated markings giving approximate volume levels on one surface of the bag. Graduated markings 52 provide approximate one thousand milliliter increments. When bag 50 is hung up using S-Hooks 46' an approximate volumetric measurement of collected fluids can be obtained. In operation, bag 50 is hung up and fluids are drained into graduated cylinders and then discarded. In this fashion, a double check on the volume accumulation can be easily obtained and most importantly, the system can remain essentially air tight. During the drainage procedure, clamp 36 may be closed and bag 50 drained leaving a small amount of fluid in tube 34'. With clamp 36' closed and bag 50 is repositioned below bag 24, and clamp opening 36 is reopened. The construction of bag 50 is preferably a white opaque back panel and a transparent front panel containing the graduated markings in a dark color.

Figure 3:
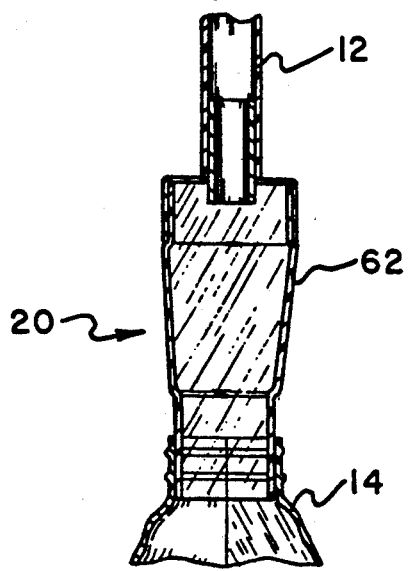
FIG. 3 is a cross-sectional view taken vertically along lines 3—3 of FIG. 1.

In the cross-sectional view of FIG. 3, device 20 is the connection of tube 12 to housing 62 which is connected directly to standard four liter urinary drainage bag 14. Device 20 constitutes the free flow of fluids through the housing normally containing an antireflux device. In device 20, the antireflux device has been removed providing free flow into bag 14. In the alternative, a standard four liter urinary drainage bag may be provided without the antireflux valve with direct connection for tube 12 into bag 14.

Figure 4:
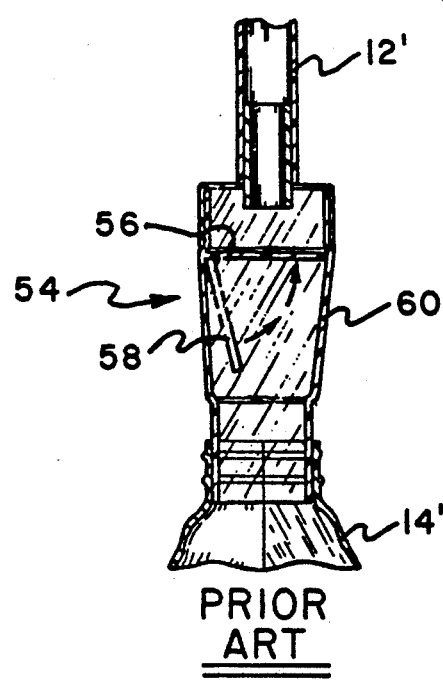
FIG. 4 is a cross-sectional view of the prior art device as shown modified in FIG. 3.

In FIG. 4, the prior art device is illustrated wherein antireflux valve device 54 includes valve flap 56 in the closed position. When fluids have not accumulated and backed up in bag 14', flap position 58 is in the open position illustrated by broken lines. The flap is held in that position by plastic memory. Housing 60 houses the antireflux valve mechanism and prevents fluids from backing up into tube 12'. Unfortunately, even this minimal restriction in flow provides ample opportunity for clotting and clogging of the device.

The twelve liter capacity of bag 24 is preferred as that capacity is somewhat larger than the amount of fluids collected within an eight hour shift. Thus, a nurse can collect the fluids, measure them and discard the fluids within his or her shift requiring minimal opening of the system. If the bag is less than twelve liters, more frequent drainage is necessary. If the capacity is greater than about twelve liters, the weight and handling of the bag becomes more inconvenient. While the twelve liter bag is most preferred, a bag in the range of eight liters to fifteen liters is satisfactory and a bag with capacity in the range of atleast about eight liters is preferred.

The Foley device is not delineated in detail as it is a standard catheter mechanism widely used in hospitals and supplied by Sherwood Medical of St. Louis, Mo., (Part #601600), Bard Products of Covington, Ga. (Part #153509), and many others. The Foley tubular device includes a drainage tube, an inlet tube providing saline solution irrigant to the bladder and a third passageway providing for passage of distilled water into the device to inflate a balloon to retain the catheter in place.

In the procedures following surgery, it is necessary to watch the fluid flow to evaluate the color of the fluid and thus the quantity of blood passing from the bladder. Since the flow is continuous, it is not necessary with the present invention to retain fluid in the Foley bag. Clearly, the capacity of the Foley bag 14 is not critical to the present invention. It is desirable to have a small capacity so that while devices 22 or 48 are being emptied, fluid can collect without backup. For that purpose, even a one liter bag is satisfactory. No tests are conducted on fluids collected from the urinary tract. The introduction of the saline solution upsets most tests and the only evaluation is the volume collected and color of the flow. As noted above, the volume is accurately determined by collection of the fluid in graduated cylinders with the preferred graduations on bag 50 providing a double check. Thus, in operation, when the bag is to be drained, closure clamp 16 is closed and bag 50 is inverted hanging on S-Hooks 46 on the side of the patient's bed. The volume in the bag is estimated using the graduated markings and recorded. Bag 50 is then drained into one thousand milliliter graduated cylinders and discarded. This procedure is much more accurate then collecting the fluids in a bucket, pouring them into cylinders and then discarding. This procedure and method essentially eliminates clotting problems.

It should be clear that additional bags 24 or 52 may be connected. An additional bag may be connected in parallel to tube 28 with a "Y" connector providing additional capacity. With clamp closures in between, the individual bags may be measured and drained separately.

While this invention has been described with reference to the specific embodiments disclosed herein, it is not confined to the details set forth and the patent is intended to include modifications and changes which may come within and extend from the following claims.

I claim:

1. A method of collecting fluids drawn from a patient's bladder using a transurethral catheter procedure, the method comprising:
   (a) inserting into the patient transurethral catheter means operatively to continuously irrigate the bladder of the patient and to continuously drain fluids from the bladder.
   (b) connecting an inlet tube of a urinary drainage collection device to the transurethral catheter means, the urinary drainage collection device comprising:
      (i) a collection bag to receive and hold a volume of fluids,
      (ii) the inlet tube connected to an inlet opening to the collection bag,
      (iii) a first drainage tube connected to a drainage outlet opening to the collection bag, and
      (iv) first closure means to open and close flow through the drainage tube,
   (c) providing that there is no antireflux device in the urinary drainage collection device to provide as high unobstructed flow as possible into the collection bag of the urinary drainage collection device,
   (d) providing a storage bag comprising:
      (i) a closed air tight capacity of at least about eight liters,
      (ii) a second inlet tube connected to an inlet opening in the storage bag,
      (iii) a second drainage tube connected to a drainage outlet opening from the storage bag, and
      (iv) second closure means to open and close flow through the second drainage tube,
   (e) connecting the second inlet tube of the storage bag to the first drainage tube of the collection bag using connecting means to connect ends of the tubes in an essentially leak proof connection,
   (f) positioning the storage bag at a height below the collection bag, and
   (g) continuously irrigating the bladder until the fluids no longer show the presence of blood.

2. The method of claim 1 wherein the drainage collection bag has a capacity of eight to fifteen liters.

3. The method of claim 2 wherein the drainage collection bag has a capacity of about twelve liters.

4. The method of claim 1 wherein the drainage collection bag has a capacity of at least ten liters.

5. The method of claim 1 wherein the connecting means to connect ends of the first inlet tube of the storage bag and the first drainage tube of the collection bag is a 5:1 tube connector.

6. The method of claim 1 further comprising:
   (a) closing the first closure means to prevent flow through the second drainage tube,
   (b) raising the storage bag to a chosen height,
   (c) opening the second closure means to drain the accumulated fluids through the second drainage tube,
   (d) measuring the quantity of the fluids drained from the storage bag,
   (e) closing the second closure means to prevent flow through the second drainage tube, and
   (f) opening the first closure means to allow flow through the second drainage tube.

7. The method of claim 6 further comprising at the closing of the second closure means to prevent flow through the second drainage tube, retaining a sufficient quantity of fluids in the second drainage tube to fill a section of the second drainage tube.

8. A device of collecting fluids drawn from a patient's bladder connectable to a transurethral catheter means operatively insertable into the patient to continuously irrigate the bladder of the patient and to continuously drain fluids from the bladder, the device comprising:
   (a) a urinary drainage collection device comprising:
      (i) a collection bag to receive and hold a volume of fluids,
      (ii) an inlet tube connected to an inlet opening to the collection bag and connectable to the transurethral catheter means,
      (iii) a first drainage tube connected to a drainage outlet opening to the collection bag, and
      (iv) first closure means to open and close flow through the drainage tube,
      wherein the urinary drainage collection device comprises no antireflux means to prevent liquid flow from the urinary drainage collection device to the transurethral resection means to provide unobstructed flow into the collection bag of the urinary drainage collection device,
   (b) connection means to connect the inlet tube of the urinary drainage collection device to the transurethral catheter means,
   (c) a storage bag device comprising:
      (i) a closed air tight storage bag of a capacity of at least about eight liters,
      (ii) a second inlet tube connected to an inlet opening in the storage bag,
      (iii) a second drainage tube connected to a drainage outlet opening from the storage bag, and
      (iv) second closure means to open and close flow through the second drainage tube,
   (d) second connection means to connect open ends of the second inlet tube of the storage bag and the first drainage tube of the collection bag in an essentially leak proof connection.

9. The device of claim 8 wherein the drainage collection bag has a capacity of about twelve liters.

10. The device of claim 8 further comprising means to hang the storage bag at a height above the floor.

11. The device of claim 8 wherein the storage bag further comprises a first edge and the inlet and outlet openings of the storage bag open proximate to the first edge, and the device further comprises means to hang the storage bag at a height above the floor with the first edge at the bottom.

12. The device of claim 11 wherein the storage bag further comprises graduated markings indicating increasing fluid volume levels in the storage bag from the first edge to an opposite edge of the storage bag.

13. The device of claim 8 wherein the second connecting means to connect ends of the inlet tube of the drainage collection bag and the drainage tube of the collection bag is a 5:1 tube adapter.

* * * * *